US012788588B2

(12) United States Patent
Atkin et al.

(10) Patent No.: US 12,788,588 B2
(45) Date of Patent: Nov. 10, 2026

(54) UNIVERSAL HANDLE

(71) Applicant: DePuy Ireland Unlimited Company, Ringaskiddy (IE)

(72) Inventors: Jamie Atkin, Leeds (GB); Lewis Butler, Leeds (GB)

(73) Assignee: DePuy Ireland Unlimited Company, Ringaskiddy (IE)

(*) Notice: Subject to any disclaimer, the term of this patent is extended or adjusted under 35 U.S.C. 154(b) by 41 days.

(21) Appl. No.: 18/962,523

(22) Filed: Nov. 27, 2024

(65) Prior Publication Data

US 2025/0169965 A1 May 29, 2025

Related U.S. Application Data

(62) Division of application No. 17/051,213, filed as application No. PCT/EP2019/061848 on May 8, 2019, now Pat. No. 12,171,673.

(30) Foreign Application Priority Data

May 10, 2018 (GB) ..................................... 1807618

(51) Int. Cl.
*A61F 2/46* (2006.01)
*A61B 17/00* (2006.01)

(52) U.S. Cl.
CPC .. *A61F 2/4607* (2013.01); *A61B 2017/00424* (2013.01); *A61B 2017/00464* (2013.01);
(Continued)

(58) Field of Classification Search
CPC ........... A61F 2/4607; A61F 2002/4619; A61B 2017/00464
See application file for complete search history.

(56) References Cited

U.S. PATENT DOCUMENTS 4,587,964 A * 5/1986 Walker ............... A61B 17/1659 606/85
5,409,492 A 4/1995 Jones
(Continued)

FOREIGN PATENT DOCUMENTS

EP 0888751 A2 1/1999
WO 2014/091454 A1 6/2014
WO 2018118316 A1 6/2018

OTHER PUBLICATIONS

PCT/EP2019/061848—International Search Report—mailed Aug. 13, 2019.
(Continued)

*Primary Examiner* — Nicholas W Woodall
(74) *Attorney, Agent, or Firm* — Barnes & Thornburg LLP

(57) ABSTRACT

There invention relates to a handle for coupling to orthopaedic surgical instruments used in joint arthroplasty. The handle is universal. The handle comprises a body having a proximal end, a distal end, and an open-ended channel extending between the distal end and the proximal end. The channel is configured for receiving a shaft of a first orthopaedic instrument such that the shaft extends completely through the handle, and the handle is in a sliding relationship with the shaft. The channel is also configured for separately and independently receiving a handle-attachment portion located at a proximal end of a second orthopaedic surgical instrument such that the handle and the second orthopaedic surgical instrument are held in a fixed relationship.

7 Claims, 7 Drawing Sheets

(52) U.S. Cl.
CPC ............... *A61B 2017/00526* (2013.01); *A61F 2002/4619* (2013.01); *A61F 2002/4627* (2013.01); *A61F 2002/4629* (2013.01); *A61F 2002/4681* (2013.01)

(56) References Cited

U.S. PATENT DOCUMENTS

| | | | | | |
|---|---|---|---|---|---|
| 5,674,225 | A * | 10/1997 | Muller | A61F 2/4607 | 606/100 |
| 6,626,913 | B1 | 9/2003 | McKinnon | | |
| 8,221,432 | B2 | 7/2012 | Smith | | |
| 11,219,536 | B2 * | 1/2022 | Arramon | A61F 2/4637 | |
| 2006/0178673 | A1 | 8/2006 | Curran | | |
| 2009/0099566 | A1 * | 4/2009 | Maness | A61F 2/4607 | 606/62 |
| 2009/0112219 | A1 | 4/2009 | Daniels | | |
| 2011/0218582 | A1 * | 9/2011 | Smith | A61F 2/4609 | 606/86 R |
| 2011/0218583 | A1 * | 9/2011 | Smith | A61B 17/56 | 606/86 R |

OTHER PUBLICATIONS

Great Britain Search Report for GB1807618.2, Oct. 17, 2018, 3 pages.

* cited by examiner

UNIVERSAL HANDLE

This is a divisional application that claims priority to U.S. patent application Ser. No. 17/051,213, which was filed on Oct. 28, 2020, which is a national stage entry of International Application No. PCT/EP2019/061848, which was filed on May 8, 2019, which claims priority to GB 1807618.2, which was filed on May 10, 2018, the entirety of each of the above-identified applications is hereby incorporated by reference.

TECHNICAL FIELD OF THE INVENTION

The present invention generally relates generally to the field of orthopaedics, and more particularly, to an instrument used to extract an implant for use in arthroplasty.

BACKGROUND TO THE INVENTION

Patients who suffer from the pain and immobility caused by osteoarthritis and rheumatoid arthritis have an option of joint replacement surgery, otherwise known as joint arthroplasty.

In hip arthroplasty, there are many different approaches, or surgical techniques for implanting the bone prostheses. For example, the posterior, anterolateral or anterior approach. Because femoral access is different with each of the aforementioned approaches, it is desirable to use different stem inserters for each approach. Depending on how the surgeon approaches the femur, or long bone, an inserter with different angular or curved configurations may be preferred so as to best reach the stem without impinging the bone or surrounding soft tissue. Surgeons may also choose different angled/curved/offset inserters depending on the anatomy of the individual patients and the selected implants. Indeed, some surgeons may also prefer to use multiple stem inserters at the varying stages of stem insertion during a single surgery.

US2009-A-0099566 discloses a kit for use in implanting a stem into a long bone. The kit includes a universal handle for locking connection to a plurality of designs of stem inserters. The stem inserters may have a standard straight shaft, a curved anterior shaft, a posterior shaft or a bullet tip shaft.

Total hip replacements (THRs) are very successful procedures, but hip revision surgery may be required to repair some or all of the components. For example, the components of the THR may wear and loosen over time as a result of normal wear and tear, a THR may repeatedly dislocate, a peri-prosthetic fracture of the bone surrounding the THR may result from a fall, or infections may develop in the THR.

For extraction of the femoral stem component, a surgeon will conventionally utilise a femoral stem extractor on which a slap hammer is slidingly assembled to repeatedly disrupt the implant/bone interface (bone bridge) of an osseointegrated implant. The femoral stem extractor is generally included in a specific instrument set for hip revision surgery, but not in the instrument kits for primary hip surgery.

Like other surgical instruments, the femoral stem extractors are housed in instrument cases that must confirm to weight and size requirements. The femoral stem extractors are bulky and can greatly reduce the available case weight and free space for other required hip arthroplasty instrumentation. The transportation, set-up, and sterilization of heavy femoral stem extractors can also become a burden to the surgical staff. Therefore, there is a need for a reduction in the size and weight of surgical instruments used in joint replacement surgeries.

SUMMARY OF THE INVENTION

The inventors have recognised that it is advantageous for a handle to be provided that is compatible with the instrumentation used both during primary joint arthroplasty surgery and also revision joint arthroplasty surgery. The provision of a universal handle reduces the inventory within the instrumentation kits, which in turn reduces cost, saves space and reduces the weight of the kit.

The invention therefore provides a universal handle that functions as a slap hammer when assembled onto a first orthopaedic instrument, and a handle when assembled onto a second orthopaedic instrument.

According to a first aspect of the invention there is provided a handle for coupling to an orthopaedic surgical instrument to be used in joint arthroplasty, the handle comprising a body comprising: a proximal end, a distal end, an open-ended channel extending between the distal end and the proximal end, the channel being configured for either receiving a shaft of a first orthopaedic instrument such that the shaft extends completely through the handle, and the handle is in a sliding relationship with the shaft; or receiving a handle-attachment portion located at a proximal end of a second orthopaedic surgical instrument such that the handle and the second orthopaedic surgical instrument are held in a fixed relationship.

Hence, the open-ended channel is configured for separately and independently receiving either a first orthopaedic instrument such that the shaft of the first orthopaedic instrument extends completely through the handle, and the handle is in a sliding relationship with the shaft, or for receiving a handle-attachment portion located at a proximal end of a second orthopaedic surgical instrument such that the handle and the second orthopaedic surgical instrument are held in a fixed relationship In some constructions, the handle comprises a locking mechanism for reversibly locking the handle to the handle-attachment portion of the second orthopaedic surgical instrument. The locking mechanism may include a spring-loaded button. However, other locking mechanisms may be utilised, and include a ball plunger, interlocking teeth, Hudson end, prongs and/or circular springs.

The locking mechanism may also function to limit the sliding movement of the handle along the longitudinal axis of the shaft of the first orthopaedic instrument.

The locking mechanism may be provided in a distally-located portion of the open-ended channel.

The first orthopaedic instrument may be a femoral stem extractor.

In some constructions, the femoral stem extractor includes a stop member disposed along the shaft. The stop member limits the sliding movement of the handle along the longitudinal axis of the shaft of the first orthopaedic instrument.

The stop member may be disposed at or adjacent to the proximal end of the shaft.

The distal end of the femoral stem extractor is provided with a means for coupling to the femoral stem. Conventionally, the distal end of the femoral stem extractor is threaded. This end makes a threaded connection with a threaded bore within the proximal surface of the femoral stem.

In some constructions, the stop member is a knob that functions not only as a stop member, but can also be gripped by the surgeon to facilitate the rotation of the shaft of the femoral stem extractor either in a clockwise or anti-clockwise direction in order to connect/disconnect the threaded distal end of the femoral stem extractor with/from the threaded bore.

In some constructions, the stop member is removably attachable to the shaft. For example the knob may be configured so that it can be threaded into the distal end of the shaft of the femoral stem extractor.

The second orthopaedic instrument may be a surgical instrument conventionally provided within an instrumentation kit for use in primary hip arthroplasty. For example, the second orthopaedic instrument may be a femoral stem inserter, a femoral canal probe or a femoral head impactor.

The femoral stem inserter may be a standard straight shaft stem inserter, a bullet tip shaft stem inserter, a curved anterior stem inserter and a posterior shaft stem inserter.

Advantageously, the handle-attachment portion of each instrument of a plurality of second orthopaedic instruments is adapted to couple with the universal handle. More advantageously, the handle-attachment portion of each instrument of a plurality of second orthopaedic instruments is identical. This facilitates the coupling of the handle-attachment portion of instruments having different functionality with the handle in an identical manner.

In some constructions, the body of the handle may include a cut-out portion dimensioned for receipt of a surgeon's fingers. Not only does this feature improve the surgeon's grip on the handle, but advantageously, the feature also reduces the weight of the handle.

According to a second aspect of the invention, there is provided a kit for use in orthopaedic surgery, the kit comprising: (i) the handle according to the first aspect of the invention; and (ii) a first orthopaedic instrument having a shaft dimensioned for receipt within the open-ended channel of the handle, such that when the first orthopaedic instrument is assembled with the handle, the handle is in a sliding relationship with the shaft, and/or a second orthopaedic instrument having a handle-attachment portion located at a proximal end thereof, such that when the second orthopaedic surgical instrument is assembled with the handle, the handle-attachment portion and the handle are held in a fixed relationship.

The first orthopaedic instrument may be a femoral stem extractor.

The second orthopaedic instrument may be a femoral stem inserter, a femoral canal probe and/or a femoral head impactor.

The femoral stem inserter may be a standard straight shaft stem inserter, a bullet tip shaft stem inserter, a curved anterior stem inserter and/or a posterior shaft stem inserter.

It is envisaged that the kit may include at least two of a second orthopaedic instrument selected from the group consisting of a femoral stem inserter, a femoral canal probe and/or a femoral head impactor.

The femoral stem inserter may be a standard straight shaft stem inserter, a bullet tip shaft stem inserter, a curved anterior stem inserter and/or a posterior shaft stem inserter.

Advantageously, the kit further comprises an impaction strike plate for removable attachment to a proximal end of the second orthopaedic instrument.

According to a third aspect of the invention, there is provided a method for preparing a surgical instrument for use in extracting a femoral stem component from a femur, the method comprising: providing the handle according to the first aspect of the invention; selecting a femoral stem extractor having a shaft and a distally-located femoral stem-attachment portion; and sliding the shaft of the femoral stem extractor through the open-ended channel of the handle such that the shaft extends beyond both the distal end and the proximal end of the handle.

In some constructions, the method may further comprise the step of removably attaching a stop member to the shaft of the femoral stem extractor at a location that is proximal with respect to the proximal end of the handle when the handle is assembled on the shaft.

If the femoral stem extractor has an integral stop member, then the user will slide the proximal end of the shaft of the femoral stem extractor into the handle through a distally-located portion of the open-ended channel and along the open-ended channel such that the proximal end of the shaft extends proximally out from the proximal end of the open-ended channel.

According to a fourth aspect of the invention there is provided a method for preparing a surgical instrument for use in inserting a femoral stem component into a femur, the method comprising: providing the handle according to the first aspect of the invention; selecting a femoral stem inserter having a proximally-located handle-attachment portion; sliding the handle-attachment portion into a distally-located portion of the open-ended channel of the handle, and locking the handle-attachment portion of the femoral stem inserter within the distally-located portion of the open-ended channel.

The locking step may include activating a spring-loaded button on the handle.

The selecting step may include selecting a femoral stem inserter from a group comprising a standard straight shaft stem inserter, a bullet tip shaft stem inserter, a curved anterior stem inserter and a posterior shaft stem inserter.

According to a fifth aspect of the invention there is provided a method for preparing a surgical instrument for use in assembling a femoral head component onto a femoral stem component, the method comprising: providing the handle according to the first aspect of the invention; selecting a femoral head impactor having a handle-attachment portion; sliding the handle-attachment portion into a distally-located portion of the open-ended channel of the handle, and locking the handle-attachment portion of the femoral head impactor within the distally-located portion of the open-ended channel.

The locking step may include activating a spring-loaded button on the handle.

According to a sixth aspect of the invention there is provided a method for preparing a surgical instrument for use in selecting a size of femoral stem component; the method comprising: providing the handle according to the first aspect of the invention; selecting a femoral canal probe having a handle-attachment portion; sliding the handle-attachment portion into a distally-located portion of the open-ended channel of the handle, and locking the handle-attachment portion of the femoral canal probe within the distally-located portion of the open-ended channel.

According to a seventh aspect of the invention there is provided a method of extracting a femoral stem component from a femur, the method comprising: providing the handle according to the first aspect of the invention; selecting a femoral stem extractor having a shaft, a distally-located stem-attachment portion and a proximally-located stop member; sliding the distal end of the shaft in a distal direction into the open-ended channel provided within the handle such that the distal end of the shaft extends beyond the distal end of the handle; inserting the stem-attachment portion of the femoral stem extractor into the femoral stem component, and sliding the handle in a proximal direction along the shaft of the femoral stem extractor to cause the proximal end of the handle to impact a distally-located surface of the stop member, thus applying an impact tension to the femoral stem component to extract it from the femur.

According to an eighth aspect of the invention there is provided a method of extracting a femoral stem component from a femur, the method comprising: providing the handle according to the first aspect of the invention; selecting a femoral stem extractor having a shaft and a distally-located stem-attachment portion; sliding the shaft of the femoral stem extractor through the open-ended channel of the handle such that the shaft extends beyond both the distal end and the proximal end of the handle; removably securing a stop member to the proximal end of the shaft of the femoral stem extractor; inserting the stem-attachment portion of the femoral stem extractor into the femoral stem component, and sliding the handle in a proximal direction along the shaft of the femoral stem extractor to cause the proximal end of the handle to impact a distally-located surface of the stop member, thus applying an impact tension to the femoral stem component sufficient to extract it from the femur.

According to a ninth aspect of the invention there is provided a method for inserting a femoral stem component into a femur, the method comprising: providing the handle according to the first aspect of the invention; selecting a femoral stem inserter having a proximally located handle-attachment portion and a distally-located stem-attachment portion; coupling the handle-attachment portion of the femoral stem inserter to a distally-located portion of the open-ended channel of the handle; inserting the stem-attachment portion of the femoral stem inserter into the femoral stem component; and applying an impaction force to the proximal end of the handle to seat the femoral stem component into the femur.

The method may further include locking the selected femoral stem inserter to the handle. The locking step may include activating a spring-loaded button on the handle.

The selecting step may include selecting a femoral stem inserter from a group comprising a standard straight shaft stem inserter, a bullet tip shaft stem inserter, a curved anterior stem inserter and a posterior shaft stem inserter.

According a tenth aspect of the invention, there is provided a method for assembling a femoral head component onto a femoral stem component, the method comprising: providing the handle of the first aspect of the invention; selecting a femoral head impactor having a proximally-located handle-attachment portion and a distally-located head impaction portion; coupling the handle-attachment portion of the femoral head impactor to a distally-located portion of the open-ended channel of the handle, contacting the head impaction portion of the femoral head impactor with a surface of a femoral head component; and applying an impaction force to the proximal end of the handle to assemble the femoral head component onto the femoral stem component.

The method may further include locking the selected femoral head impactor to the handle. The locking step may include activating a spring-loaded button on the handle.

According an eleventh aspect of the invention, there is provided a method of selecting a size of femoral stem component; the method comprising: providing the handle of the first aspect of the invention; selecting a femoral canal probe having a proximally-located handle-attachment portion; coupling the handle-attachment portion of the femoral canal probe to a distally-located portion of the open-ended channel of the handle; inserting the canal probe into a femoral canal.

The method may further include locking the selected femoral canal probe to the handle. The locking step may include activating a spring-loaded button on the handle.

BRIEF DESCRIPTION OF THE DRAWINGS

For a more complete understanding of the present invention and the advantages thereof, reference is now made to the following description taken in connection with the following drawings, in which.

DETAILED DESCRIPTION OF THE DRAWINGS

Embodiments of the present invention and the advantages thereof are best understood by referring to the following descriptions and drawings, wherein like numerals are used for like and corresponding parts of the drawings.

Figure 1:
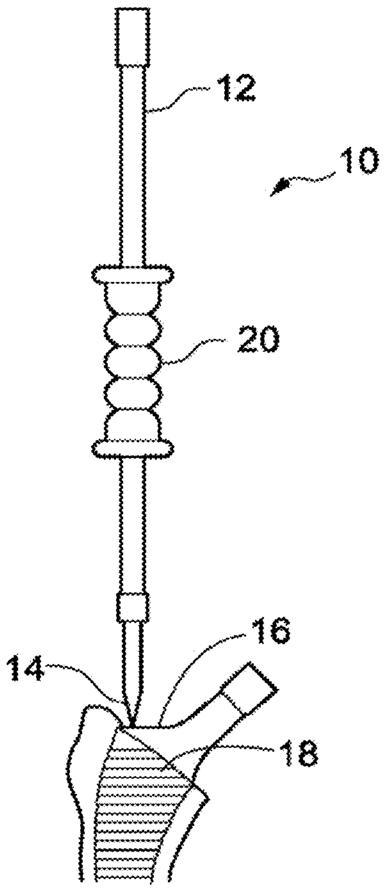
FIG. 1 is a schematic of a conventional stem extractor.

Referring to FIG. 1, there is shown a conventional femoral stem extractor 10 which includes a shaft 12 with a threaded distal end 14 for connection into a threaded bore (not shown) in the proximal surface 16 of a femoral stem 18. A slap hammer 20 is slidingly received on the shaft. In use, a surgeon repeatedly pulls the slap hammer upwards with a towards a strike plate (not shown). The impaction force generated as the slap hammer strikes the lower surface of the strike plate is transmitted downwardly along the shaft to repeatedly disrupt the implant/bone interface (bone bridge) of an osseointegrated implant.

Figure 2:
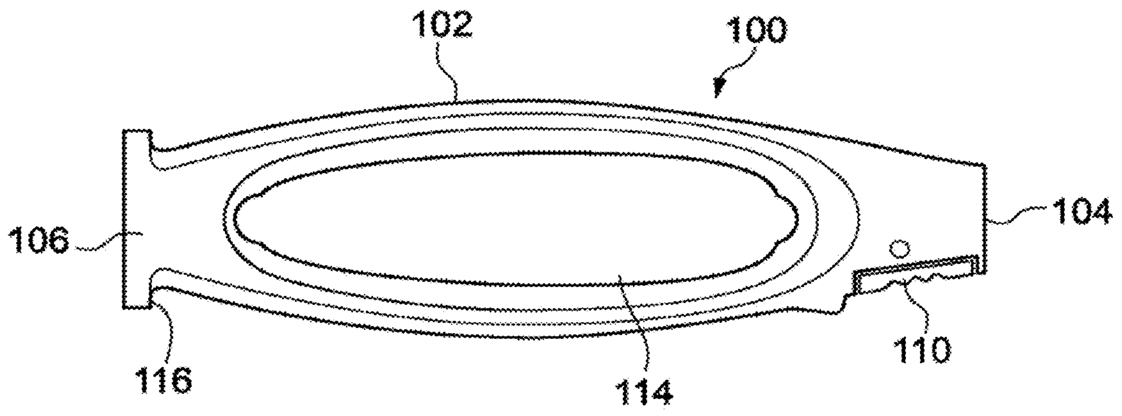
FIG. 2 is a perspective view of the handle of the present invention.

FIG. 2 shows the universal or modular handle 100 of the present invention. The handle includes a body 102 having a distal end 104 and a proximal end 106. An open-ended channel 108 (not shown) extends between the distal end and the proximal end. The channel is configured for receiving a shaft of a first orthopaedic instrument such that the shaft extends completely through the handle, and the handle is in a sliding relationship with the shaft. The channel 108 is also configured for receiving a handle-attachment portion located at a proximal end of a second orthopaedic surgical instrument such that the handle and the second orthopaedic surgical instrument are held in a fixed relationship. The handle also includes a locking mechanism, shown here in the form of a spring-loaded button 110. The spring-loaded button includes a stop pin (not shown).

Advantageously, the handle is ergonomically designed to improve a surgeon's grip on the handle. In the construction shown, the body of the handle may include a cut-out section 114. Advantageously, this cut-out section is dimensioned to receive a surgeon's fingers. In use, a surgeon may insert his/her fingers through the cut-out section and wrap them about the adjacent portion of the body in order to facilitate gripping of the handle.

In some further constructions, as shown in FIG. 2, the handle may include an impaction strike plate 116 at the proximal end. The strike plate may be in the form of a flange.

The handle is preferably monolithic. In some constructions, the handle 100 is manufactured from a metal material suitable for medical applications. For example, the metal could be stainless steel.

In some other constructions, the handle might also be made of a plastic. The plastic may or may not contain reinforcement and could be ABS, polypropylene, polyurethane, polyesters, acetals, or polyimide. This is a representative list and does not exclude other plastics or polymer systems that are used for medical applications.

It is envisaged that the handle may be 3-D printed.

Figure 3:
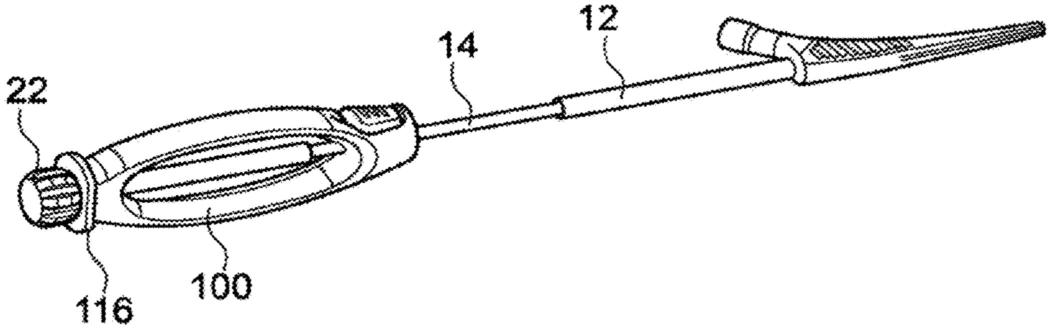
FIG. 3 is a perspective view of the handle of the present invention assembled onto a first construction of a femoral stem extractor.
Figure 4:
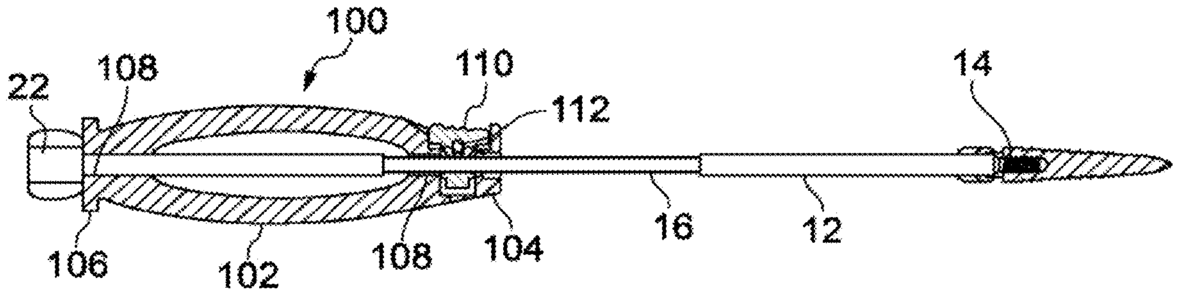
FIG. 4 is an internal assembled view of the assembly shown in FIG. 3.

Turning to FIGS. 3 and 4, the handle 100 of the present invention is shown assembled onto the shaft component 12 of a femoral stem extractor 10.

The shaft component 12 of the femoral stem extractor is a cylindrical component with a generally circular cross-section. The shaft component may also be referred to as a stem extractor rod.

The shaft component 12 includes a threaded distal end 14, a waist portion 16 and a stop member 22.

The threads on the threaded distal end 14 are complementary to the threads of a threaded bore in the proximal surface of the femoral stem. Hence, the threaded distal end 14 functions as the means to connect the shaft component of the stem extractor to the femoral stem component.

The waist portion 16 allows the handle to travel along the shaft. This is because the waist portion is dimensioned such that when the handle is assembled with the shaft component, there is a clearance between the stop pin 112 component of the spring-loaded button and the external surface of the shaft.

The stop member 22 functions to limit the direction of travel of the handle 100 in a proximal direction, and additionally as an extraction strike plate. The stop member is shown in this embodiment as a knob that is configured to be threaded into the proximal end of the shaft component 12. The knob includes circumferentially distributed grooves to improve the surgeons grip.

To assemble the slap hammer stem extractor, the user depresses the spring-loaded button 110 on the handle. The user then slides the shaft component 12 into, through, and then out of the open-ended channel 108 of the body 102 of the handle 100.

In constructions in which the stop member 22 is permanently fixed to the proximal end of the shaft, the distal threaded end 14 of the shaft must be is inserted into the channel 108 in a direction from the proximal end 106 of the body 102 to the distal end 104 of the body.

In constructions in which the stop member 22 is removably attachable to the proximal end of the shaft, the shaft may be inserted into the channel 108 either in a proximal or distal direction of travel. The stop member is then attached to the proximal end of the shaft.

The user releases the spring-loaded button 110 once the button is located at a position along the waist portion 16 of the shaft. The handle 100 is then free to run axially along the smaller diameter of the shaft component defined by the waist portion.

Next, the user aligns the threaded distal end 14 of the shaft component with the threaded bore located within the proximal surface of the femoral stem component.

The user then grips and turns the stop member 22 in order to form a screw-threaded connection between the shaft component of the femoral stem extractor and the femoral stem component.

To disrupt the osseointegration of the femoral stem component and the bone, the user grips the handle and then repeatedly and forcibly slides the handle in a proximal direction such that a proximal (top) surface of the strike plate 116 strikes the distal (bottom) surface of the stop member 22. This results in a step-wise extraction of the femoral stem component out of the femoral bone.

Figure 5:
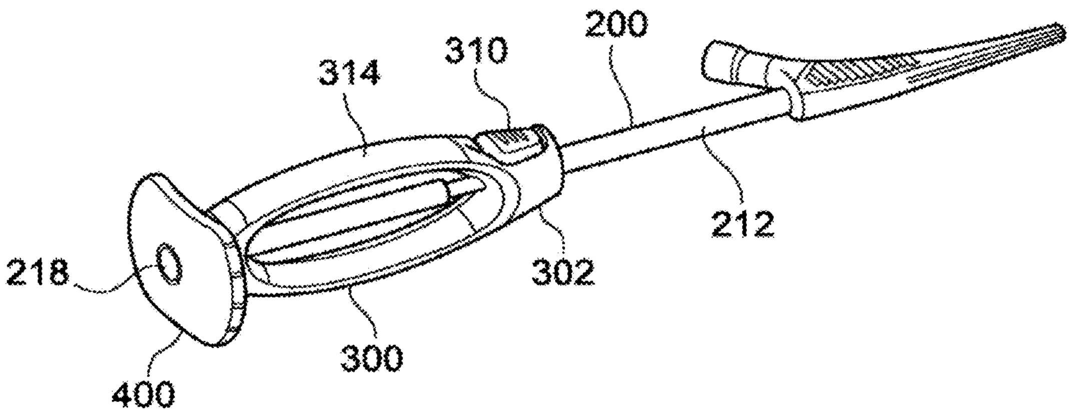
FIG. 5 is a perspective view of the handle of the present invention assembled onto a second construction of a femoral stem extractor.
Figure 6:
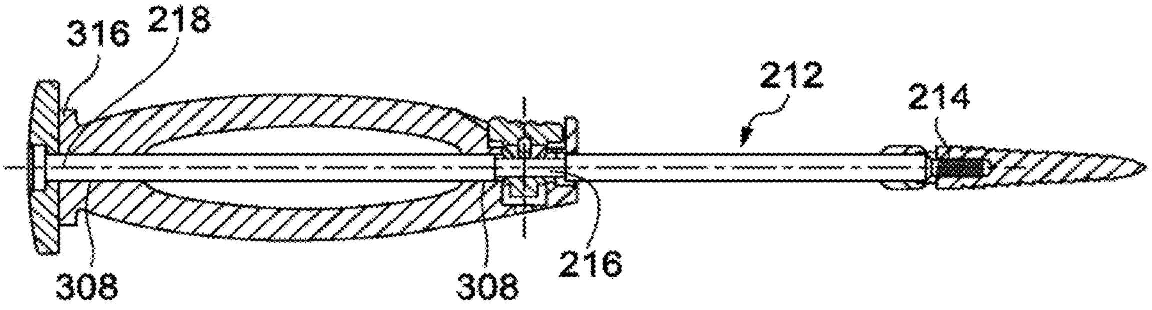
FIG. 6 is an internal assembled view of the assembly shown in FIG. 5.
Figure 7A:
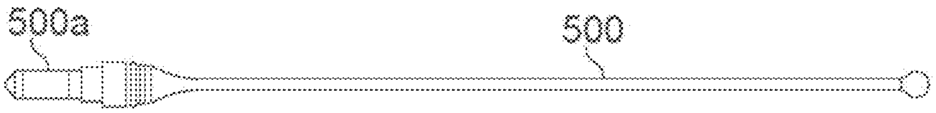
FIGS. 7A-7F are schematics illustrating examples of instruments used in the implantation of a femoral stem implant to which the handle of the present invention may be assembled.
Figure 7B:
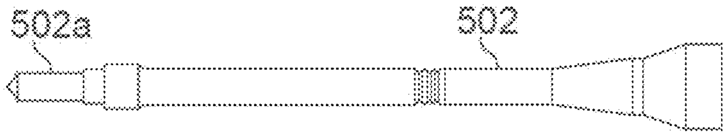
Figure 7C:
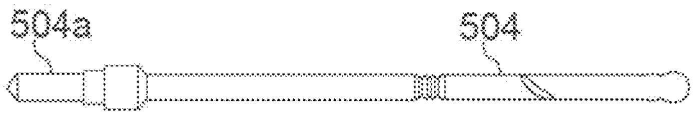
Figure 7D:
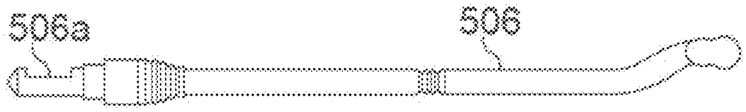
Figure 7E:
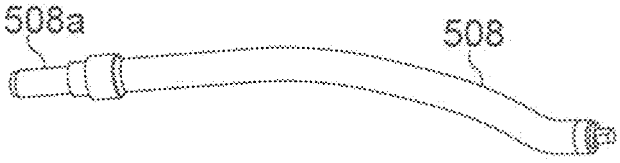
Figure 7F:
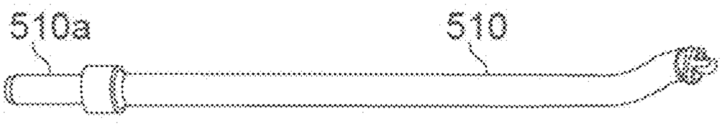

Now turning to FIGS. 5 and 6, the handle 300 of the present invention is shown assembled onto the shaft component 212 of a second construction of a femoral stem extractor 200.

The shaft component 212 of the femoral stem inserter is a cylindrical component with a generally circular cross-section.

The shaft component 212 includes a threaded distal end 214, a waist portion 216 and a proximal end 218. The threads on the threaded distal end 214 are complementary to the threads of a threaded bore in the proximal surface of the femoral stem. Hence, the threaded distal end 214 functions as the mechanism to connect the shaft component of the stem extractor to the femoral stem component.

To assemble the femoral stem extractor 200 with the handle 300, the user depresses the spring-loaded button 310 on the handle. The user then slides the shaft component 212 into, through, and then out of the open-ended channel 308 of the body 302 of the handle 200.

The user releases the spring-loaded button 310 once the button is located at a position along the waist portion 216 of the shaft. The handle 300 is then locked onto the shaft, whilst allowing free rotation of the shaft.

In the construction shown, an impaction/extraction strike plate 400 is welded to the proximal end 218 of shaft 212.

In other constructions, the strike plate 400 and shaft 212 may be manufactured as a monobloc component.

In still further constructions, the impaction/extraction strike plate 400 may be removably secured to the proximal end 218 of the shaft 212 by the user. The strike plate may be assembled with the proximal end of the shaft of the femoral stem inserter either before or after the shaft has been slid through the handle 300.

Various means of removably securing the impaction/extraction strike plate 400 to the shaft will be known to the skilled artisan, and may include a threaded connection, or an interference fit, also known as a press fit or friction fit.

To extract the femoral stem component from the bone, the user again grips the handle 300 and repeatedly and forcibly slides the handle in a proximal direction such that a proximal (top) surface of the strike plate 316 strikes the distal (bottom) surface of the impaction/extraction strike plate 400. This results in a step-wise extraction of the femoral stem component out of the femoral bone.

FIGS. 7A-7F illustrate examples of the second orthopaedic instrument on which the handle may be assembled, these include, but are not limited to: (a) a femoral canal probe 500, (b) a femoral head impactor 502, (c) a standard straight shaft inserter 504, (d) a bullet tip shaft 506, (e) a posterior shaft stem inserter 508, and (f) a curved anterior stem inserter 510. Each shaft of the instruments shown has an identical proximally-located handle-attachment portion 500*a*, 502*a*, 504*a*, 506*a*, 508*a*, and 510*a*. In the constructions shown here, the handle-attachment portion is a connection flat that engages with a connection flat on the modular handle button. Because each handle-attachment portion is of the same design, each shaft can be locked into the same handle depending on the type of surgery or the surgeon preference.

Although particular constructions of the invention have been described, it will be appreciated that many modifications/additions and/or substitutions may be made within the scope of the claimed invention.

The invention claimed is:

1. A method for preparing a surgical instrument for use in extracting a femoral stem component from a femur, the method comprising:

providing a handle, the handle comprising:

a body comprising:

a proximal end, a distal end, and an open-ended channel extending between the distal end and the proximal end, the channel being configured for either receiving a shaft of a first orthopaedic instrument such that the shaft extends completely through the handle, and the handle is in a sliding relationship with the shaft, or receiving a handle-attachment portion located at a proximal end of a second orthopaedic instrument such that the handle and the second orthopaedic instrument are held in a fixed relationship;

selecting a first orthopaedic instrument having a shaft and a distally-located femoral stem-attachment portion; and sliding the shaft of the first orthopaedic instrument through the open-ended channel of the handle such that the shaft extends beyond both the distal end and the proximal end of the handle.

2. The method of claim 1, further comprising removably attaching a stop member to the shaft of the first orthopaedic instrument at a location that is proximal with respect to the proximal end of the handle when the handle is assembled on the shaft.

3. A method for preparing a surgical instrument for use in inserting a femoral stem component into a femur, the method comprising:

providing a handle, the handle comprising:

a body comprising:

a proximal end, a distal end, and an open-ended channel extending between the distal end and the proximal end, the channel being configured for either receiving a shaft of a first orthopaedic instrument such that the shaft extends completely through the handle, and the handle is in a sliding relationship with the shaft, or receiving a handle-attachment portion located at a proximal end of a second orthopaedic instrument such that the handle and the second orthopaedic instrument are held in a fixed relationship;

selecting a second orthopaedic instrument having a proximally-located handle-attachment portion;

sliding the handle-attachment portion into a distally-located portion of the open-ended channel of the handle, and locking the handle-attachment portion of the second orthopaedic instrument within the distally-located portion of the open-ended channel.

4. The method of claim 3, wherein the locking step includes activating a spring-loaded button on the handle.

5. The method of claim 3, wherein the selecting step includes selecting a femoral stem inserter from a group comprising a standard straight shaft stem inserter, a bullet tip shaft stem inserter, a curved anterior stem inserter and a posterior shaft stem inserter.

6. The method of claim 3, wherein:

the second orthopaedic instrument is selecting a femoral head impactor having a proximally-located handle-attachment portion; and with the handle-attachment portion of the femoral head impactor locked within the distally-located portion of the open-ended channel, the surgical instrument is configured for use in assembling a femoral head component onto a femoral stem component.

7. The method of claim 3, wherein:

the second orthopaedic instrument is a femoral canal probe; and with the handle-attachment portion of the femoral canal probe locked within the distally-located portion of the open-ended channel, the surgical instrument is configured for use in selecting a size of femoral stem component.

* * * * *